US010123610B2

(12) United States Patent
Doll et al.

(10) Patent No.: US 10,123,610 B2
(45) Date of Patent: Nov. 13, 2018

(54) FORCE-SENSING TOOTHBRUSH

(71) Applicant: The Gillette Company, Boston, MA (US)

(72) Inventors: Alexander Franz Doll, Nürnberg (DE); Stefan Hubert, Olching (DE); Florian Kiener, Rieden (DE); Karin Lutz, München (DE); Robert Schuetz, Wiesbaden (DE)

(73) Assignee: THE GILLETTE COMPANY LLC, Boston, MA (US)

( * ) Notice: Subject to any disclaimer, the term of this patent is extended or adjusted under 35 U.S.C. 154(b) by 293 days.

(21) Appl. No.: 14/971,452

(22) Filed: Dec. 16, 2015

(65) Prior Publication Data
US 2016/0174699 A1 Jun. 23, 2016

Related U.S. Application Data

(60) Provisional application No. 62/094,609, filed on Dec. 19, 2014.

(51) Int. Cl.
A46B 15/00 (2006.01)
A61C 17/00 (2006.01)
A61C 17/16 (2006.01)
A46B 11/00 (2006.01)
(Continued)

(52) U.S. Cl.
CPC ........ *A46B 15/0012* (2013.01); *A46B 11/002* (2013.01); *A46B 15/004* (2013.01); *A46B 15/0008* (2013.01); *A46B 15/0046* (2013.01); *A61C 17/16* (2013.01); *A46B 11/0034* (2013.01); *A46B 11/0037* (2013.01);
(Continued)

(58) Field of Classification Search
CPC ............ A46B 15/0012; A46B 15/0008; A46B 15/004; A46B 15/0046; A46B 11/002; A61C 17/16
See application file for complete search history.

(56) References Cited

U.S. PATENT DOCUMENTS 2,682,066 A * 6/1954 Keely .................... A61C 17/32
15/167.2
3,284,829 A 11/1966 Allen
3,623,175 A 11/1971 Emerson
(Continued)

FOREIGN PATENT DOCUMENTS

CN 101741169 6/2010
CN 103859784 6/2014

OTHER PUBLICATIONS

International Search Report with written opinion, dated Mar. 14, 2016, 20 pages.

*Primary Examiner* — Weilun Lo
(74) *Attorney, Agent, or Firm* — Vladimir Vitenberg

(57) ABSTRACT

A toothbrush comprises a head including a plurality of cleaning elements attached to the head, a handle, a neck extending between the head and the handle, a motor unit including a motor and a manual winder for manually energizing the motor, and a force sensor configured to detect a user-applied force exceeding a predetermined threshold force, wherein the force sensor causes the toothbrush to produce at least one of an audible signal and a tactile signal when the user-applied force exceeds a predetermined threshold force. An audible signal and a tactile signal may comprise, respectively, muting of the motor and interruption of vibration of the toothbrush.

12 Claims, 5 Drawing Sheets

(51) Int. Cl.
 *A61C 17/22* (2006.01)
 *F03G 1/02* (2006.01)
(52) U.S. Cl.
 CPC ..... *A46B 2200/1066* (2013.01); *A61C 17/221* (2013.01); *F03G 1/02* (2013.01)

(56) References Cited

U.S. PATENT DOCUMENTS

| | | | |
|---|---|---|---|
| 3,945,076 A * | 3/1976 | Sung | A61C 17/40 15/22.1 |
| 4,253,212 A * | 3/1981 | Fujita | A46B 15/0002 15/167.1 |
| 4,476,604 A * | 10/1984 | White | A46B 15/0002 15/105 |
| 4,802,255 A | 2/1989 | Breuer et al. | |
| 5,268,005 A | 12/1993 | Suhonen | |
| 5,282,291 A * | 2/1994 | Spieler | A46B 5/0062 15/105 |
| 5,313,909 A | 5/1994 | Tseng et al. | |
| 5,722,106 A | 3/1998 | Masterman et al. | |
| 5,836,769 A | 11/1998 | Spencer | |
| 5,880,532 A * | 3/1999 | Stopher | B60K 6/10 290/1 C |
| 5,980,542 A | 11/1999 | Saldivar | |
| 6,018,840 A | 2/2000 | Guay et al. | |
| 6,058,541 A | 5/2000 | Masterman et al. | |
| 6,081,957 A * | 7/2000 | Webb | A46B 15/0002 15/105 |
| 6,102,923 A | 8/2000 | Murayama | |
| 6,151,745 A | 11/2000 | Roberts et al. | |
| 6,327,734 B1 * | 12/2001 | Meginniss, III | A46B 15/0002 15/105 |
| 6,402,768 B1 | 6/2002 | Liebel | |
| 6,412,137 B1 * | 7/2002 | Heidari | A46B 9/12 15/105 |
| 6,475,553 B2 | 11/2002 | Guay et al. | |
| 6,536,068 B1 * | 3/2003 | Yang | A46B 15/0002 15/105 |
| 6,553,604 B1 | 4/2003 | Braun et al. | |
| 7,383,603 B2 | 6/2008 | Edwards | |
| 8,544,131 B2 | 10/2013 | Braun et al. | |
| 9,565,927 B2 | 2/2017 | Bloch et al. | |
| 2004/0134007 A1 | 7/2004 | Davies | |
| 2004/0154112 A1 | 8/2004 | Braun et al. | |
| 2004/0255416 A1 | 12/2004 | Hohlbein | |
| 2005/0000004 A1 | 1/2005 | Yun | |
| 2005/0000043 A1 | 1/2005 | Chan et al. | |
| 2005/0003846 A1 | 1/2005 | Anderson | |
| 2005/0108841 A1 | 5/2005 | Edwards | |
| 2005/0166344 A1 | 8/2005 | Hohlbein | |
| 2005/0210612 A1 | 9/2005 | Hohlbein et al. | |
| 2006/0010628 A1 | 1/2006 | Moskovich | |
| 2006/0026784 A1 | 2/2006 | Moskovich et al. | |
| 2006/0052806 A1 | 3/2006 | Xi et al. | |
| 2006/0080794 A1 | 4/2006 | Punshon | |
| 2006/0104456 A1 * | 5/2006 | Filo | A61C 17/221 381/77 |
| 2006/0195995 A1 | 9/2006 | Moskovich et al. | |
| 2006/0272112 A9 | 12/2006 | Braun et al. | |
| 2007/0049956 A1 | 3/2007 | Mythen | |
| 2007/0140959 A1 | 6/2007 | Park et al. | |
| 2007/0251040 A1 | 11/2007 | Braun et al. | |
| 2008/0078044 A1 * | 4/2008 | Savage | A46B 5/0058 15/167.1 |
| 2008/0189888 A1 | 8/2008 | Hohlbein | |
| 2008/0244849 A1 | 10/2008 | Moskovich et al. | |
| 2009/0243405 A1 * | 10/2009 | Luo | A61C 17/3418 310/38 |
| 2009/0320227 A1 * | 12/2009 | Cohen | A46B 15/0002 15/167.1 |
| 2010/0325828 A1 | 12/2010 | Braun et al. | |
| 2011/0016651 A1 * | 1/2011 | Piserchio | A46B 5/007 15/167.1 |
| 2012/0160261 A1 * | 6/2012 | Harden | A46B 11/0027 132/311 |
| 2012/0198640 A1 * | 8/2012 | Jungnickel | A46B 15/0012 15/105 |
| 2016/0192769 A1 | 7/2016 | Bloch et al. | |

* cited by examiner

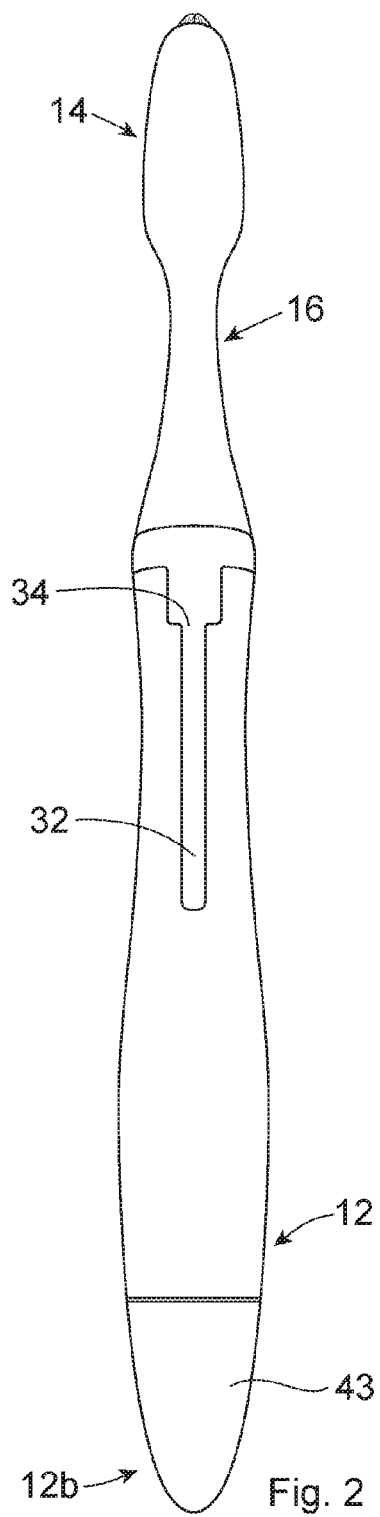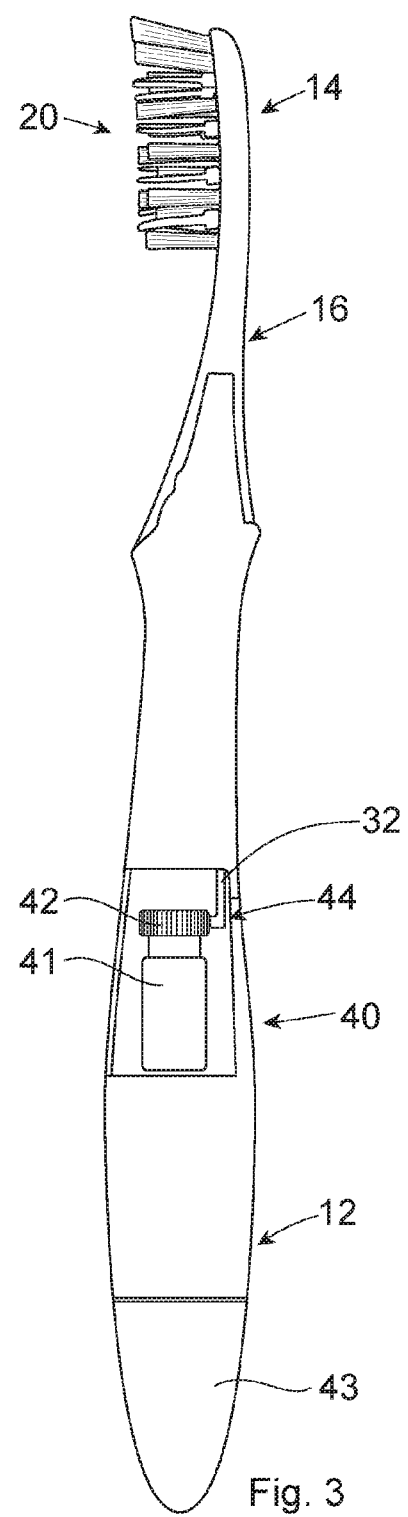

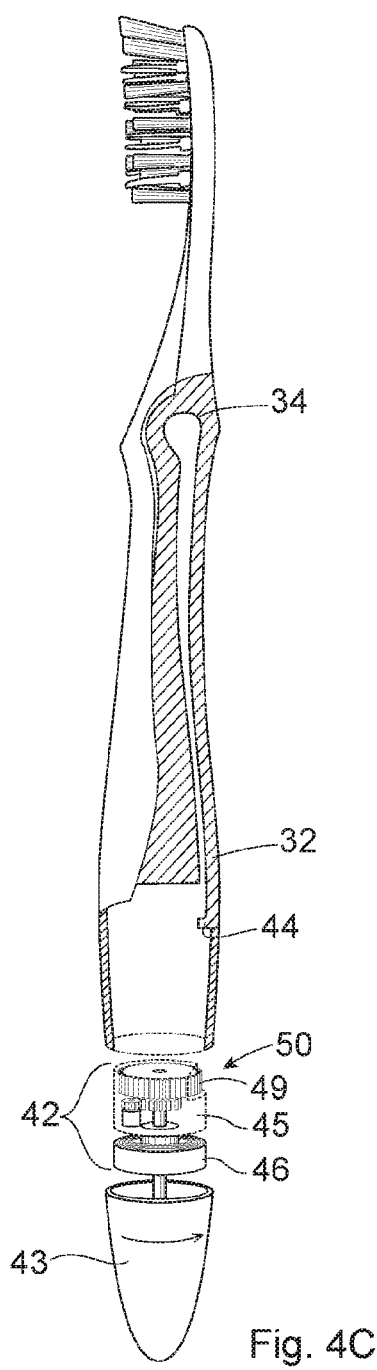
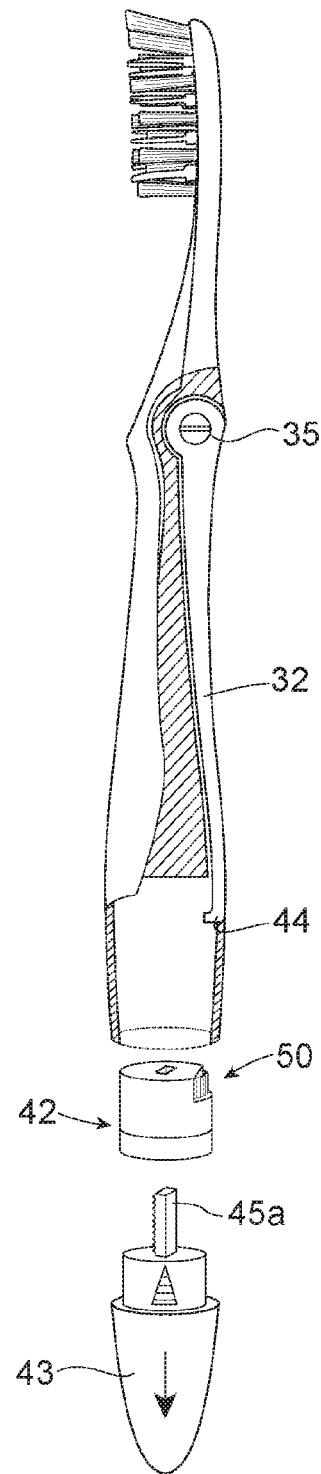
Fig. 4C
Fig. 5A

FORCE-SENSING TOOTHBRUSH

FIELD OF THE INVENTION

The present disclosure is directed to a toothbrush, and more particularly to a toothbrush including a force-indication system.

BACKGROUND OF THE INVENTION

The utilization of toothbrushes to clean one's teeth has long been known. During the brushing process, a user generally applies a force to the brush, which force is ultimately applied, the cleaning elements of the toothbrush, against the user's teeth and gums. While a minimal force can be sufficient to remove plaque and debris, some users tend to apply higher-than-required levels of force, which may lead to negative oral-health consequences for an individual, including, e.g., gum irritation and ultimately recession, as well as tooth-enamel abrasion. Unfortunately, because some users may feel that those conditions stem from poor cleaning, in an effort to "correct" the situation, the users may apply even more force during brushing—which in turn may exacerbate the above-mentioned negative effects. In addition, studies have shown that the cleaning ability of a toothbrush may be reduced if brushing force is increased beyond the optimal level.

To avoid or mitigate these undesirable effects, some dental professionals recommend the use of a soft-bristled toothbrush. But the use of a soft-bristled toothbrush may not always preclude the application of high brushing forces to the teeth and gums. Furthermore, it may be extremely difficult for an individual to determine the optimal force required for cleaning. While a user may believe that she applies a minimal level of force to enable cleaning, feeling the level at which the real force is too high is sometimes difficult.

Aside from brushing force, proper brushing takes at least two minutes. Although toothbrushes having timers are known, most of inexpensive, manual brushes do not have those.

Accordingly, a need exists for an inexpensive, easy-to-use toothbrush that does not rely on electric power or complex mechanics to signal to the user when the applied brushing force is too high and when the brushing has been performed for the proper duration.

SUMMARY OF THE INVENTION

These and other features, aspects and advantages of specific embodiments will become evident to those skilled in the art from a reading of the present disclosure.

The toothbrush of the invention comprises a head including a plurality of cleaning elements attached to the head, a handle, and a neck extending between the head and the handle. The handle has a first end adjacent to the neck and a second free end opposite to the first end. The handle can conveniently have an internal chamber in which a motor unit is disposed. The motor unit includes a motor and a motor energizer, such as, e.g., a manual motor winder, for manually energizing the motor.

The toothbrush includes a force sensor structured and configured to detect a user-applied force exceeding a predetermined threshold force. The force sensor is structured to cause the toothbrush to produce at least one of an audible signal and a tactile signal when the user-applied force exceeds a predetermined threshold force. The force sensor can comprise a deflectable extension bar having a first end and a second end, wherein the first end is connected to a body of the toothbrush, and a second end is free.

In one embodiment, the first end of the deflectable bar is connected to a body of the toothbrush via a living hinge. Then, at least one of the deflectable bar and the living hinge can be integrally formed with the handle. In another embodiment, the first end of the deflectable bar is connected to a body of the toothbrush via a torsion element, e.g., a bar or a pin.

The force sensor may comprise or be connected to a blocking assembly including a stop gear in operative communication with the stop pin. The stop gear is also in operative communication with the motor. The stop pin can be disposed at the free end of the deflectable bar and extending into a body of the toothbrush. The stop gear can be (but does not have to be) incorporated into a gear box, located in the brush's body and comprising several gears translating a winding movement of the winder into energizing the motor. Thus, the stop gear can be structured and configured to be in operative communication with the motor and the stop pin.

The manual winder can be conveniently incorporated into an end cap disposed at the second end of the brush's handle. In one embodiment, the manual winder comprises a rotatable structure. A user can activate the motor by rotating the end cap, by a certain degree, relative to the rest of the brush. In another embodiment, the manual winder comprises a pull-out structure. A user can activate the motor by pulling out the end cap winder, to a certain distance, relative to the rest of the brush.

In operation, when the force applied by the user is too high, the force sensor causes the motor to stop. This occurs because the extension bar, under an applied force that is higher than a threshold force, deflects from its rest position into the body of the brush, thereby causing the stop pin to move forward, thereby engaging the stop gear. Once the rotation of the stop gear is blocked, the motor, which is in operative communication with the stop gear, stops as well. When this occurs, at least one of an audible signal and a tactile signal, such as, e.g., vibration of the toothbrush, would indicate muting of the motor.

In another embodiment, the toothbrush can be equipped with a timer, to program a length of a brushing cycle. The timer can be disposed in the internal chamber of the handle. The timer can be in operative communication with the motor, to be activated by the winder for a set period of time, as is described herein. In one embodiment, e.g., the end cap, comprising the winder, can be manually rotated by the user for a user-determined number of degrees to energize the motor and activate the timer for the set period of time. In another embodiment, the end cap, comprising the winder, can be manually pulled out for a user-determined distance to energize the motor and activate the timer for the set period of time. In either instance, the desired length of brushing cycle can be conveniently indicated on the body of the brush, either for rotation or for pulling out.

These and other features, aspects and advantages of specific embodiments will become evident to those skilled in the art from a reading of the present disclosure.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 2 is a schematic plan back view of the toothbrush shown in FIG. 1;

FIG. 3 is a schematic side view, in partial cross-section, of the toothbrush shown in FIG. 1;

FIG. 4C is an embodiment of the toothbrush similar to that shown in FIGS. 4A and 4B, and schematically showing a rotating wind-up mechanism comprising gears and a spring.

FIG. 5A is a schematic side view of an embodiment of a toothbrush according to one or more embodiments illustrated and described herein and comprising a pull-out wind-up mechanism.

DETAILED DESCRIPTION OF THE INVENTION

Figure 1:
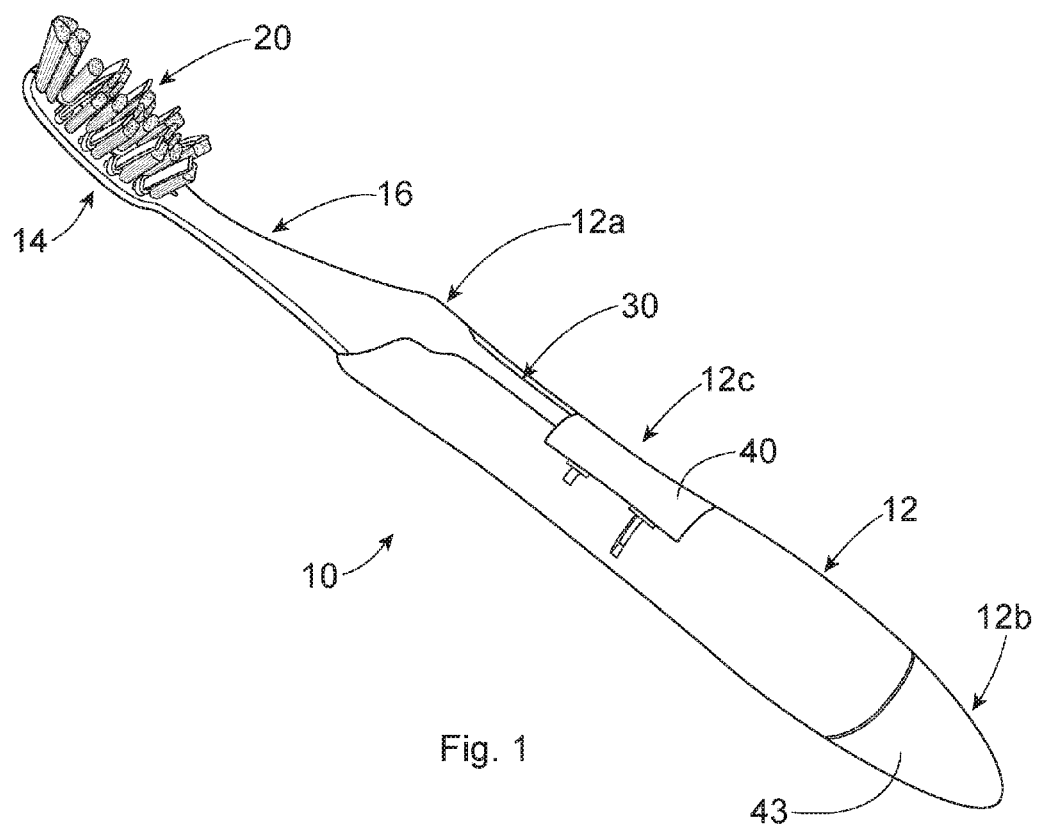
FIG. 1 is a schematic perspective view of a toothbrush according to one or more embodiments illustrated and described herein.

The following text sets forth a broad description of numerous different embodiments of the present invention. The description does not purport describe every possible embodiment since describing every possible embodiment would be impractical, if not impossible. It is to be construed, therefore, as exemplary only. A skilled artisan will readily understand that any feature, characteristic, component, composition, ingredient, product, and step or methodology described herein can be deleted, combined with, or substituted for, in whole or in part, any other feature, characteristic, component, composition, ingredient, product, and step or methodology described herein. Numerous similar or alternative embodiments could be implemented, using either current technology or technology developed after the filing date of this application, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this disclosure (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Lastly, unless a claim element is defined by reciting the word "means" and a function without the recital of any structure, it is not intended that the scope of any claim element be interpreted based on the application of 35 U.S.C. § 112, sixth paragraph.

For ease of explanation, the toothbrush described hereafter shall be a manual toothbrush. The present disclosure, however, is not limited to manual toothbrushes; it can be applicable to power/electrical toothbrushes as well. Additionally, the present disclosure may be equally applicable to other personal-hygiene implements, such as, e.g., blades, razors, and the like.

As schematically shown in several exemplary embodiments herein, a toothbrush 10 includes a handle 12, a head 14, and a neck 16 extending between the handle 12 and the head 14. A plurality of cleaning elements 20 can be attached to the head 14. The brush 10 includes a force sensor 30. The force sensor 30 can be adjacent to the neck 16. The force sensor 30 can include an extension element 32 connected to a living hinge 34, as is schematically shown in the embodiment of FIG. 4C. Alternatively, the extension element 32 can be connected to a torsion element 35, comprising e.g., a pin or a bar, as is schematically shown in FIG. 5A. One skilled in the art will understand that other suitable connections, known in the art (and not illustrated herein), between the first end of the extension element 32 and a body of the brush can be employed as well.

The extension element 32 can be disposed on the brush's front side (FIG. 1) or on the brush's back side (FIGS. 2 and 3)—and can comprise a relatively thin, deflectable bar connected to the brush's body for a movement relative to the brush's body. One embodiment of the extension element 32 includes a cantilever-type bar connected to the brush's body with a hinge 34, such as, e.g., a living hinge, and deflecting under the user-applied force from the bar's in-rest position and relative to the body of the handle 12. In the exemplary embodiments shown, the extension element 32 deflects, at least partially, into a body of the handle 12. The force sensor 30, including the extension element 32 and the hinge 34, may be integrally formed with the handle 12. Alternatively, the force sensor 30, including the extension element 32 and the hinge 34, may comprise several elements structured and configured to form a mechanical connection among them.

The handle 12 has a first end 12a, a second end 12b, and an internal chamber 12c formed inside the handle 12 between the first and second ends 12a, 12b (FIG. 1). A motor unit 40, located in the internal chamber 12c, comprises a motor 41 and a motor energizer 42 for manually energizing the motor 41 (FIG. 3). The motor unit 40 may include any assembly to energize and control the motor 41, as is known in the art. The motor 41 may be of any suitable type, including, e.g., a spring motor.

The motor energizer 42 may comprise a winder 43 and a stop pin 44. The winder 43 can be in operative communication with gears 45, including a rack gear 45a (FIGS. 5A, 5B), and a constant-force spring (also known as a "clock spring") 46. The constant-force spring 46 can typically be made of a band or tape of steel wrapped around itself a desired number of times to create a spiral. The spring, if wound, can store energy that can be released by causing the spring unwound. The unwinding spring creates a rotational force that releases, over time, a constant amount of load. A stop pin 44 can be structured and configured to be in contact with a blocking assembly 50, which can be part of the motor unit 40. The stop pin 44 can be integrally formed with the extension bar 32 and adjacent to the free end thereof. In one embodiment, the stop pin comprises the free end of the extension element 32. Alternatively, the stop pin 44 can be configured to comprise a separate (from the extension element 32) structure in contact with the free end of the extension element 32. In the latter instance, the extension element 32 can be configured to be in constant contact with the stop pin 44—or, alternatively, can be configured to be at a distance from the stop pin 44 when the brush is not being used but contact and move the pin under an application of the user-induced force. These embodiments can be easily visualized by one skilled in the art—and therefore are not illustrated in exact detail herein.

Various known interaction mechanisms can be used to allow a user to energize and otherwise control the motor 40. Non-limiting examples include a winding key, a pull cord, a lever, a sliding mechanism, a mechanism that winds up the motor when pressing the brush in a holder or stand, or any other suitable mechanism. For example, by winding the spring 46, a user can energize the spring-powered motor 41. In one exemplary embodiment, shown in FIGS. 4A-4C, a user can rotate the brush's end cup comprising the winder 43 to impart energy into the spring-powered motor 41. In another exemplary embodiment, shown in FIGS. 5A and 5B, a user can energize the motor 41 by pulling out the end cup comprising the winder 43.

Figure 4A:
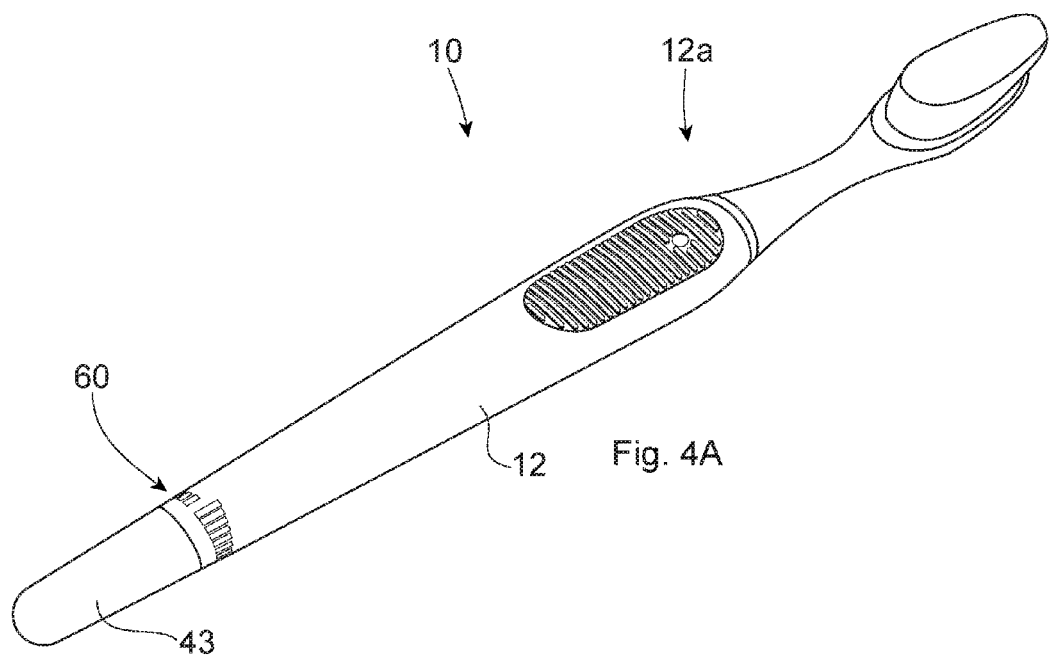
FIG. 4A is a schematic perspective view of another embodiment of the toothbrush according to one or more embodiments illustrated and described herein.
Figure 4B:
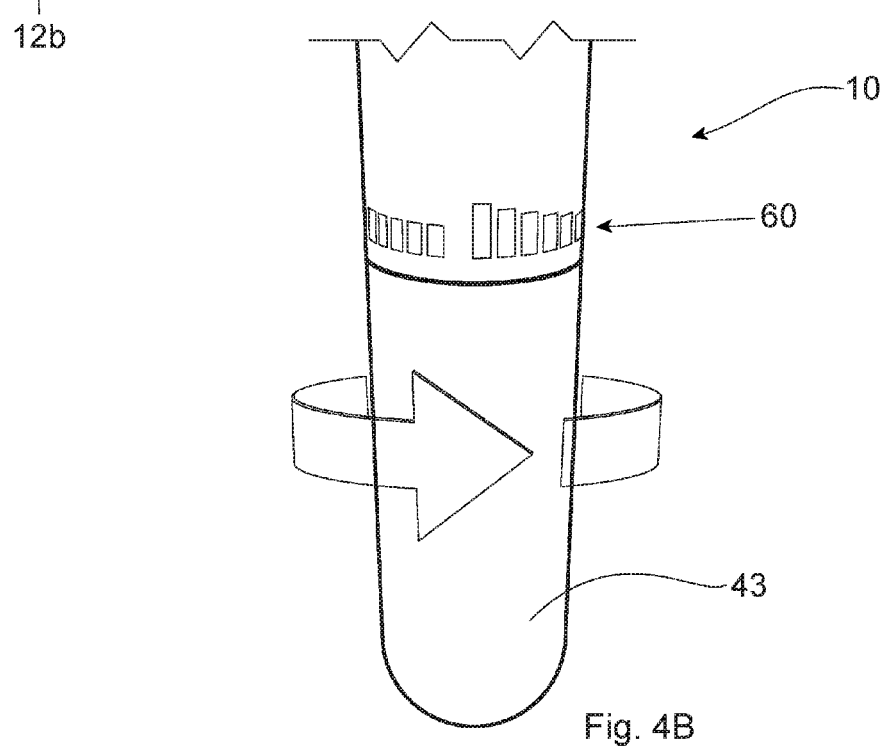
FIG. 4B is a schematic elevated fragmental view of the toothbrush of FIG. 4A and showing a rotating wind-up mechanism including a time scale.

The motor 40 may further include a timer 60, including a time scale (best shown in FIGS. 4A, 4B and 5B), such as, e.g., a count-down timer, by which the user can program a time period for a brushing cycle. For example, as shown in FIGS. 4A and 4B, the user can twist or rotate the winder 43, comprising in that embodiment an end cap of the handle 12, to energize the motor and also to set or adjust the brushing time. Thus, to start the timer 60, the user can rotate the winder 43 by a certain number of degrees and according to a scale that can be marked on the brush 10. The user can, e.g., rotate the winder 43 by 180 or 360 degrees, which in turn will energize the motor 40 and set up the brushing cycle to a predetermined amount of time.

In one exemplary embodiment, a predetermined amount of time may correspond to the number of degrees turned; 90 degrees, e.g., may correspond to a 30-second brushing cycle, while 360 degrees may correspond to a 2-minute cycle. In another exemplary embodiment, 120 degrees may correspond to a 60-second brushing cycle. In yet another exemplary embodiment, 150 degrees may correspond to a 90-second brushing cycle. In still another exemplary embodiment, 180 degrees may correspond to a 120-second brushing cycle. Generally, the timer 60 can be structured to be set for any amount of time, e.g., from about 5 seconds to about 180 seconds. The user, by rotating the winder 43 by a certain number of degrees according to a scale marked on the brush 10, will be able to energize the motor 41 for any desired length of the brushing cycle. At the completion of a brushing cycle, the motor 41 stops.

Figure 5B:
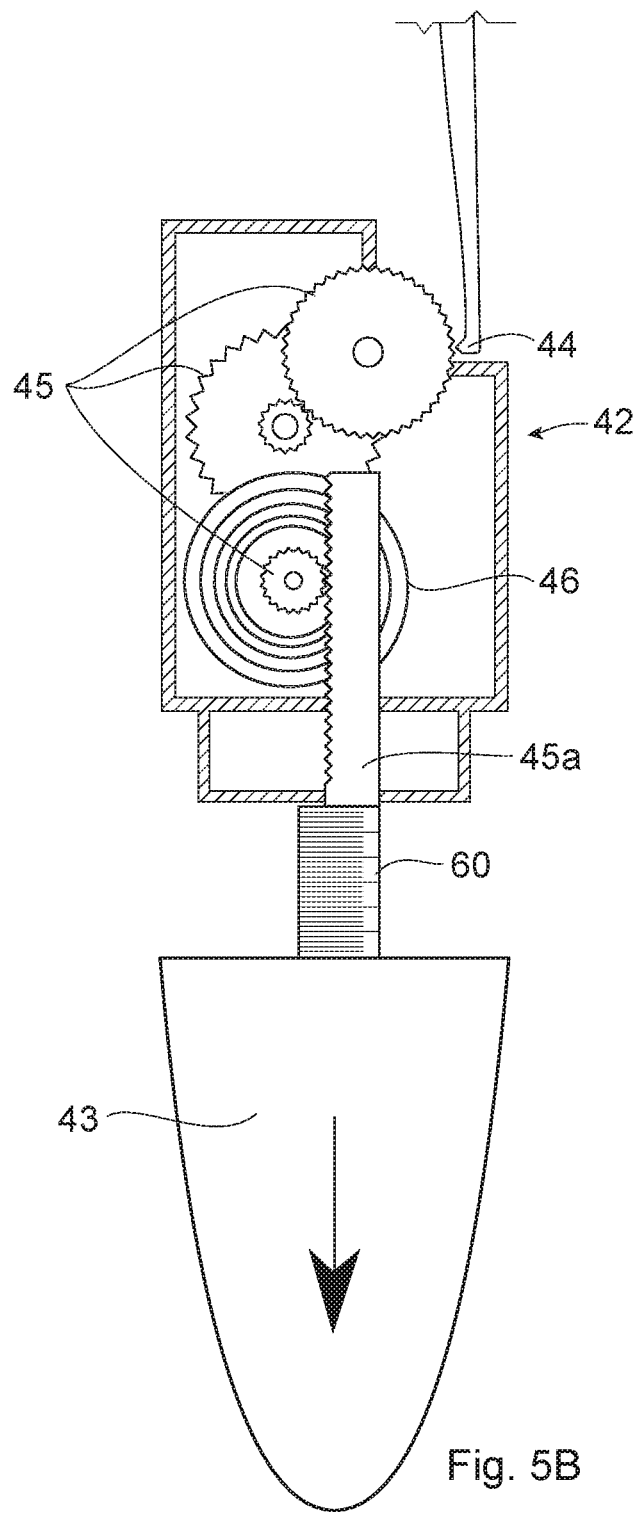
FIG. 5B is an elevated cross-sectional fragmental view of the toothbrush of FIG. 5A and showing a wind-up mechanism including a time scale.

In another exemplary embodiment, shown in FIGS. 5A and 5B, the brush 10 comprises a pull-out timer mechanism. A user can pull out the winder 43 to energize the motor 41 and also to set or adjust the brushing time. To start the timer 60, the user pulls out the end cap of the brush to a certain distance indicated by a time scale marked on the brush. This distance corresponds to a predetermined amount of time that defines a brushing cycle or a portion of the brushing cycle. For example, a distance of 5 mm may correspond to a 30-second brushing time, while a distance of 20 mm may correspond to a 2-minute brushing time. In another exemplary embodiment a distance of 10 mm may correspond to a 90-second brushing time, while a distance of 15 mm may correspond to a 2-minute brushing time. In yet another exemplary embodiment 14 mm may correspond to a 120-second brushing time. The timer 60 can be structured to be set for any amount of time, e.g., from about 5 seconds to about 180 seconds. By pulling out the winder 43 to a certain distance according to the marked scale, the user will be able to energize the motor 41 for any desired length of the brushing time/cycle. At the completion of the brushing cycle, the motor 41 stops.

In operation, the user can energize the motor 41 as is described herein. In the exemplary embodiments shown in FIGS. 4C and 5B, the user, by rotating the winder 43 (FIG. 4C) or pulling of the winder 43 (FIG. 5B), will cause winding of a drive spring 46. Once the spring motor 41 is sufficiently wound/energized to deliver a desired brushing cycle, the toothbrush 10 is in condition for operation. Then, the user can place the cleaning elements 20 in contact with the user's teeth and start the brushing cycle, e.g., by pressing a start button or otherwise, as is known in the art. For example, the toothbrush 10 may include a user-operated button or switch that can allow the user to start/stop the brushing cycle.

In one exemplary embodiment, the motor 41, including the gears associated therewith, may be structured to produce a distinctive sound to signal to the user that the brushing cycle has started and/or continues. In addition or in alternative to sound, the motor 41 may be structured to cause the toothbrush 10 to vibrate. To this end, in some embodiments additional special gears can be used to generate a specific sound to communicate to the user the brush's operational stages. Vibration also can be used to signal to the user the beginning and/or end of the brushing cycle. In some embodiments, an unbalanced weight can be utilized to cause microvibrations in the brush—to communicate desired brushing-cycle information to the user.

During brushing, a high application force imparted to the cleaning elements 20 causes the extension element 32 of the force sensor 30 to move in the direction of motor 41. As long as the applied force is below or equal to a predetermined threshold force, the movement of the extension element and that of the associated stop pin 44 is not sufficient enough to cause an interruption of the brushing cycle—and the brushing cycle continues. If the applied force is higher that the predetermined threshold force, the extension element 32 moves towards a blocking assembly 50 (FIG. 5A), thereby moving or engaging the stop pin 44. The stop pin 44 is in operative communication with the motor's blocking assembly 50, which can comprise, e.g., a stop gear 49 (FIG. 4C). When the force imparted on the extension bar 32, and consequently the stop pin 44, is too high, the stop pin 44 moves and engages the blocking assembly, which in its turn causes the motor 41 to stop running As a result, the user gets a clear audible signal, i.e., muting of the motor, indicating that the user has applied force exceeding the desired brushing force. In addition, the stoppage of the motor 41 naturally causes the toothbrush to cease vibrating, thus providing to the user a tactile signal, also indicating that the applied brushing force is too high.

The timer 60 can be structured to hold or pause during the stoppage period of time, so that the time during which the applied force remains higher than the threshold force is not being counted towards the brushing cycle. In this embodiment, once the user decreases the applied brushing force below the threshold force, the motor 41 and the timer 60 will continue running until either the brushing cycle is completed or the user once again applies a brushing force that is too high.

In some exemplary embodiments, a value of an applied excessive brushing force may be greater than or equal to about 1 Newton, 1.25 Newtons, 1.5 Newtons, 1.75 Newtons, 2.00 Newtons, 2.10 Newtons, 2.20 Newtons, 2.30 Newtons, 2.40 Newtons, 2.50 Newtons, 2.60 Newtons, 2.75 Newtons, 2.85 Newtons, greater than or equal to about 3.00 Newtons, greater than or equal to about 3.50 Newtons, greater than or equal to about 3.75 Newtons, greater than or equal to about 4.00 Newtons, greater than or equal to about 4.25 Newtons, greater than or equal to about 4.50 Newtons, greater than or equal to about 4.75 Newtons, greater than or equal to about 5.00 Newtons, greater than or equal to about 5.25 Newtons, greater than or equal to about 5.50 Newtons, greater than or equal to about 5.75 Newtons, or greater than or equal to about 6.00 Newtons.

In some exemplary embodiments, a value of an applied low or normal force may be less than or equal to about 5.00 Newtons, about 4.75 Newtons, about 4.5 Newtons, about 4.25 Newtons, about 4.00 Newtons, about 3.75 Newtons, about 3.5 Newtons, about 3.25 Newtons, about 3.00 Newtons, about 2.75 Newtons, about 2.50 Newtons, about 2.25 Newtons, about 2.00 Newtons, about 1.75 Newtons, about 1.50 Newtons, about 1.25 Newtons, about 1.00 Newtons, about 0.75 Newtons, or about 0.50 Newtons. In some exemplary embodiments, values for a low end of a sufficient force range, an upper end of the sufficient force range, and/or the sufficient force range may be selected from any of the values provided above with regard to the excessive force and/or low or normal force conditions.

The handle region 12 may be constructed of any suitable material, such as, e.g., polypropylene, nylon, high density polyethylene, other moldable stable polymers, and any combinations thereof. In some embodiments, at least one of the handle 12, the neck 16, and the head 14 may be formed from a first material and include recesses, channels, grooves, and the like for receiving a second material different from the first material. For example, the handle may include an elastomeric grip region or a plurality of elastomeric grip regions. The elastomers among the plurality of elastomeric grip features may comprise similar materials or different materials with respect to, e.g. color, hardness, elasticity, porosity, surface energy, and the like, and any combination thereof.

As used herein, the term "cleaning elements" refers to any suitable element which can be inserted into the oral cavity for the purpose of brushing the surface of the teeth and/or cleaning the tongue, and/or massaging the gums. Examples of suitable elements include bristle tufts, elastomeric massage elements, elastomeric cleaning elements, massage elements, tongue cleaners, soft tissue cleaners, hard surface cleaners, combinations thereof, and the like. The head 14 may comprise a variety of cleaning elements. For example, the head 14 may comprise bristles, abrasive elastomeric elements, elastomeric elements in a particular orientation or arrangement, e.g., pivoting fins, prophy cups, or the like. Several suitable examples of elastomeric cleaning elements and/or massaging elements are described, e.g., in U.S. Patent Application Publication Nos. 2007/0251040; 2004/0154112; 2006/0272112; and in U.S. Pat. Nos. 6,553,604; 6,151,745. The cleaning elements may be tapered, notched, crimped, dimpled, or the like. Some suitable examples of these cleaning elements and/or massaging elements are described in U.S. Pat. Nos. 6,151,745; 6,058,541; 5,268,005; 5,313,909; 4,802,255; 6,018,840; 5,836,769; 5,722,106; 6,475,553; and U.S. Patent Application Publication No. 2006/0080794.

The cleaning elements may be attached to the head 14 in any suitable manner. Conventional methods include stapling, anchor free tufting, and injection mold tufting. Cleaning elements comprising an elastomer may be formed integral with one another, e.g., they may be formed outwardly extending from an elastomeric base portion integrally formed with the cleaning elements.

The head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Disclosures of all documents cited herein, including any cross referenced or related patents or applications, are hereby incorporated herein by reference in their entirety, unless expressly excluded or otherwise limited. The citation of any document is not an admission that it is prior art with respect to any invention disclosed or claimed herein—or that it alone, or in any combination with any other reference or references, teaches, discloses, or suggests, any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A toothbrush comprising:
   a handle having a first end, a second end opposite to the first end, and an internal chamber disposed between the first and second ends;
   a head coupled to the first end of the handle, the head including a plurality of cleaning elements;
   a neck extending between the head and the handle;
   a spring motor disposed in the internal chamber;
   a timer disposed in the internal chamber, the timer being in operative communication with the spring motor;
   a force sensor structured and configured to detect a user-applied force exceeding a predetermined threshold force and to cause an activation of at least one of an audible signal and a tactile signal indicating that the force applied by a user exceeds the threshold force;
   a manual winder comprising an end cap coupled to and movable relative to the first end of the handle;
   wherein the end cap is structured and configured to be manually moved, by a user, to energize the motor and activate the timer for a set period of time.

2. The toothbrush of claim 1, wherein the end cup is structured and configured to be manually rotated, by the user, for a user-determined number of degrees to energize the motor and activate the timer for the set period of time.

3. The toothbrush of claim 1, wherein the end cup is structured and configured to be manually pulled out, by the user, to a user-determined distance to energize the motor and activate the timer for the set period of time.

4. The toothbrush of claim 1, wherein the at least one of an audible signal and a tactile signal comprises at least one of muting of the motor and interruption of vibration of the toothbrush.

5. The toothbrush of claim 1, wherein the toothbrush comprises a blocking assembly for causing the motor to stop when the force sensor detects that the user-applied force exceeds the predetermined threshold force.

6. The toothbrush of claim 1, wherein the force sensor comprises an extension bar having a first end and a second end, wherein the first end is connected to a body of the toothbrush, and the second end is in operative communication with a stop pin.

7. The toothbrush of claim 6, wherein the second end of the extension bar comprises the stop pin disposed thereon.

8. The toothbrush of claim 5, wherein the blocking assembly comprises a stop gear in operative communication with the motor and the stop pin.

9. The toothbrush of claim 1, wherein the force sensor comprises an extension bar having a first end and a second end, wherein the first end is connected to a body of the toothbrush, and a second end is free.

10. The toothbrush of claim 9, wherein the first end of the extension bar is connected to a body of the toothbrush via a living hinge.

11. The toothbrush of claim 10, wherein the extension bar and the living hinge are integrally formed with one another.

12. The toothbrush of claim 9, wherein the first end of the extension bar is connected to a body of the toothbrush via a torsion element comprising a bar or a pin.

* * * * *